(12) United States Patent
Deville et al.

(10) Patent No.: US 12,385,842 B2
(45) Date of Patent: Aug. 12, 2025

(54) QUANTIFICATION OF WELLBORE FLUID ADDITIVES BY LASER INDUCED BREAKDOWN SPECTROSCOPY

(71) Applicant: Halliburton Energy Services, Inc., Houston, TX (US)

(72) Inventors: Jay Deville, Spring, TX (US); Preston Andrew May, Porter, TX (US); Sandeep Kumar Borra, Tomball, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 18/388,021

(22) Filed: Nov. 8, 2023

(65) Prior Publication Data

US 2025/0146945 A1 May 8, 2025

(51) Int. Cl.
*G01N 21/71* (2006.01)
*E21B 49/08* (2006.01)
*G01N 33/28* (2006.01)

(52) U.S. Cl.
CPC .......... *G01N 21/718* (2013.01); *E21B 49/08* (2013.01); *G01N 33/2823* (2013.01)

(58) Field of Classification Search
CPC ...... E21B 49/005; E21B 21/066; E21B 21/01; E21B 49/00; E21B 21/06; E21B 49/08; E21B 49/10; E21B 49/087; E21B 47/135; E21B 49/003; E21B 49/081; E21B 49/088

See application file for complete search history.

(56) References Cited

U.S. PATENT DOCUMENTS

| | | | |
|---|---|---|---|
| 7,530,265 B2 | 5/2009 | Difoggio | |
| 9,103,176 B2 | 8/2015 | Delmar et al. | |
| 10,436,865 B2 | 10/2019 | Washburn | |
| 11,543,557 B2 | 1/2023 | Teotonio Da Silva | |
| 2016/0108687 A1 | 4/2016 | Rapoport | |

FOREIGN PATENT DOCUMENTS

| | | | | |
|---|---|---|---|---|
| AU | 2014277680 A1 | * | 10/2015 | ............. E21B 21/06 |
| CA | 2948362 C | * | 9/2018 | ............. E21B 49/00 |
| WO | 2019167030 A1 | | 9/2019 | |
| WO | WO-2021181145 A1 | * | 9/2021 | ............. E21B 49/02 |

* cited by examiner

*Primary Examiner* — Zakiya W Bates
(74) *Attorney, Agent, or Firm* — Kilpatrick Townsend & Stockton LLP

(57) ABSTRACT

Additives of wellbore fluids can be quantified using laser induced breakdown spectroscopy. For example, a method can involve acquiring a sample of wellbore fluid from a wellbore. The wellbore fluid can include an additive. The sample can be processed to separate the wellbore fluid into a liquid sample and a solid sample. A laser induced breakdown spectroscopy device can identify a chemical composition of the liquid sample or the solid sample. A concentration of the additive in the wellbore fluid can be determined based on the chemical composition of the liquid sample or the solid sample. An adjustment to a composition of the wellbore fluid can be performed based on the concentration of the additive in the wellbore fluid.

9 Claims, 4 Drawing Sheets

QUANTIFICATION OF WELLBORE FLUID ADDITIVES BY LASER INDUCED BREAKDOWN SPECTROSCOPY

TECHNICAL FIELD

The present disclosure relates generally to wellbore operations and, more particularly (although not necessarily exclusively), to quantification of wellbore fluid additives by laser induced breakdown spectroscopy.

BACKGROUND

A well system (e.g., oil or gas) may include a wellbore drilled through a subterranean formation. During the drilling of a subterranean well system, a fluid may circulate through a fluid circulation system that includes a drilling rig and fluid treatment and storage equipment located at or near a surface of a well. The fluid may be pumped by a fluid pump through an interior passage of a drill string, through a drill bit, and back to the surface through an annulus between a wellbore and the drill string. As the well is drilled, fluids, including gases and liquids from the subterranean formation, may be released and captured as the fluid is circulated.

DETAILED DESCRIPTION

Figure 1:
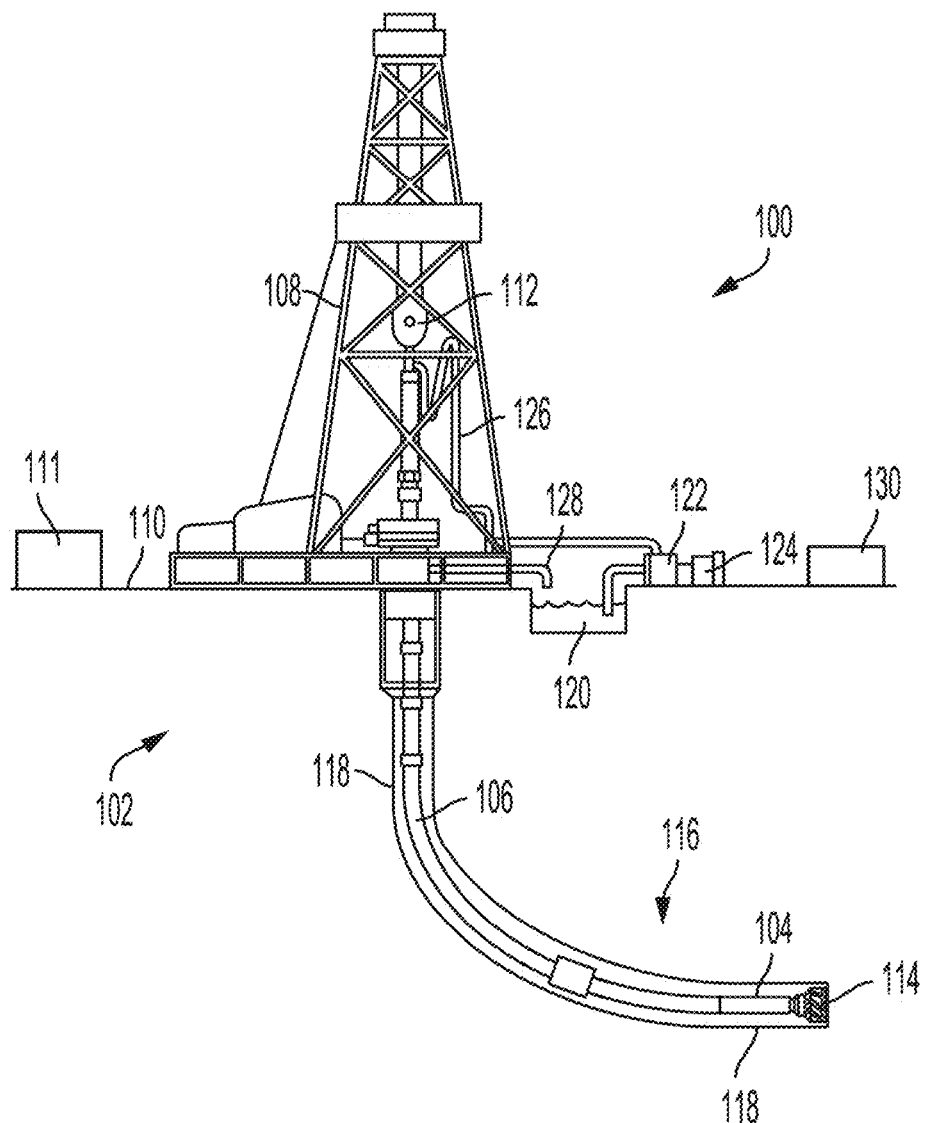
FIG. 1 is a cross-sectional view of a well system for quantifying additives in wellbore fluid using laser induced breakdown spectroscopy according to one example of the present disclosure.

Certain aspects and examples of the present disclosure relate to techniques for quantifying additives in wellbore fluid using laser induced breakdown spectroscopy (LIBS) at a wellsite. Samples of wellbore fluid, such as active drilling fluid, can be processed and subjected to LIBS onsite to determine concentrations of chemical additives. For example, a LIBS device can use a laser pulse to form a plasma that atomizes and excites the processed sample. The excitation can cause the processed sample to emit light that can be detected by the LIBS device as a spectrum of optical data. The optical data can be analyzed to produce a detailed compositional analysis of the processed sample. Such onsite analysis of wellbore fluids can allow additive concentration adjustments to be made in real time.

The concentration of additives in wellbore fluid may be known initially but may change downhole as fluid circulates. Each additive may have a particular function in the wellbore fluid. Maintaining that function, for example in an active, circulating drilling fluid, may involve maintaining an effective concentration of the additive. Uncertainty of the additive concentration can increase risk of losing or diminishing the function of the additives in the drilling fluid. In some cases, performance tests, such as testing a viscosity of the drilling fluid to check performance of viscosifiers, may give an indication of some additive concentrations. But performance tests may not provide an accurate quantification of many additives in drilling fluid. Additionally, many performance tests may not be performed onsite, or results may be lagging indicators (e.g., by the time a performance test indicates an issue, it may be too late to correct the concentration). Typical concentration tests may be more accurate than performance tests but many may not be performed onsite or may be lacking for a number of regularly used additives.

In contrast, embodiments of the present disclosure can be performed onsite to quantify additives by detecting elemental composition and chemical fingerprinting of processed samples by taking LIBS measurements. Better understanding of wellbore fluid composition can result in better wellbore fluid maintenance and improved wellbore fluid performance. Both overtreatment and undertreatment of additives can be avoided. This can allow for easier maintenance of wellbore fluids in the field, such as during drilling operations, and can also allow for easier treatment and re-use of wellbore fluids that are returned to mud tanks after use downhole. Embodiments of the present disclosure can also be used to detect compounds or elements found in any additive. For example, LIBS can be used to detect all common elements, including lower atomic mass elements such as sulfur or below that may be difficult to detect using conventional techniques.

In a particular example, a drilling fluid that is actively circulating in a wellbore may include additives injected into the drilling fluid at a surface of the wellbore. While in the wellbore, the drilling fluid may capture liquids, gases, cuttings, or other materials from the subterranean formation. The additives in the drilling fluid may interact with the materials from the subterranean formation. When materials (e.g., cuttings) are separated and removed from the drilling fluid at the surface of the wellbore, additives that have interacted with the materials may also be removed from the drilling fluid. This may adjust concentration of the additives in the drilling fluid, which may reduce effectiveness of some additives. The updated additive concentration of the active drilling fluid can be determined using LIBS. For example, a sample of drilling fluid is acquired and processed (e.g., filtered or centrifuged) to separate into a solid phase and a liquid phase. The liquid phase may still include nanoparticles suspended in the liquid sample.

Once the sample has been acquired and processed, the sample can be analyzed using a LIBS device. Either the solid phase or the liquid phase of the sample can be analyzed. The LIBS device can be pointed at the sample to perform a LIBS measurement. In some examples, the LIBS measurement can be targeted to a particular element of interest or to a chemical fingerprint of a compound or product (e.g., of an additive). The LIBS measurement can be used to quantify an amount or concentration of a particular additive in the drilling fluid. If the amount or concentration of the particular additive is determined to be below a threshold amount, the function of the additive may have a reduced effect in the drilling fluid. Mitigation operations can then be performed to correct the low concentration of the additive. For example, the LIBS measurement can indicate that little to no emulsifiers are present in the active drilling fluid, so additional emulsifier can be injected into the drilling fluid. The amount of additional emulsifier injected into the drilling fluid can depend on the concentration of emulsifier detected by the LIBS device in the sample. In this way, quantification of additives in wellbore fluids can be performed onsite at the wellbore to allow adjustments to wellbore fluids to be made in real time relative to the LIBS measurement.

In some examples, some additives may be tagged for improved detection by the LIBS device. For example, none of the additives injected into drilling fluid may initially include fluorine. To increase detectability, a viscosifier can be tagged with fluorine atoms during polymerization. The tagged viscosifier can be injected into the drilling fluid. Later, a sample of the drilling fluid can be processed. A LIBS device can acquire a LIBS measurement for the processed sample. Any fluorine detected in the LIBS measurement can be associated with the viscosifier. The amount or concentration of fluorine in the sample can therefore indicate the amount or concentration of viscosifier in the sample. In some examples, tagging an additive with an element that is otherwise not present in the drilling fluid may result in more accurate quantification of additives compared to detection of compounds typically present in the additives. This is because different additives injected into the drilling fluid may have elements or compounds in common.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a cross-sectional view of a well system 100 for quantifying additives in wellbore fluid using laser induced breakdown spectroscopy (LIBS) according to one example of the present disclosure. A wellbore 118 used to extract hydrocarbons may be created by drilling into a subterranean formation 102. The well system 100 may include a bottom hole assembly (BHA) 104 positioned or otherwise arranged at the bottom of a drill string 106 extended into the subterranean formation 102 from a derrick 108 arranged at the surface 110. The derrick 108 includes a kelly 112 used to lower and raise the drill string 106. The BHA 104 may include a drill bit 114 operatively coupled to a tool string 116, which may be moved axially within the drilled wellbore 118 as attached to the drill string 106. The combination of any support structure (in this example, derrick 108), any motors, electrical equipment, and support for the drill string 106 and tool string 116 may be referred to herein as a drilling arrangement.

During operation, the drill bit 114 can penetrate the subterranean formation 102 to create the wellbore 118. The BHA 104 can provide control of the drill bit 114 as the drill bit 115 advances into the subterranean formation 102. The combination of the BHA 104 and drill bit 114 can be referred to as the drilling tool. Fluid or "drilling mud" from a mud tank 120 may be pumped downhole using a mud pump 122 powered by an adjacent power source, such as a prime mover or motor 124. The drilling mud may be injected with additives that provide various functions in the drilling mud. Examples of the additives can include shale inhibitors, fluid loss additives, viscosifiers or suspension aides, corrosion inhibitors, emulsifiers, bridging agents, weighting agents, salts, glycols, silicates, nanoparticles, loss circulation materials, lubrications, or any other suitable additives.

The drilling mud may be pumped from the mud tank 120 through a stand pipe 126, which feeds the drilling mud into the drill string 106 and conveys the same to the drill bit 114.

The drilling mud exits one or more nozzles (not shown) arranged in the drill bit 114 and in the process cools the drill bit 114. After exiting the drill bit 114, the drilling mud can circulate back to the surface 110 via the annulus defined between the wellbore 118 and the drill string 106. While in the wellbore 118, the drilling mud may capture liquids and gases from the subterranean formation 102, particulates or cuttings generated by the drill bit 114 engaging with the subterranean formation 102, or a combination thereof. When the drilling mud circulates back to the surface 110, hole cleaning can occur which involves returning the drill cuttings and debris to the surface 110. The cuttings and mixtures can be passed through a flow line 128 and can be processed such that a cleaned mud is returned downhole through the stand pipe 126 once again.

In some examples, a sample of drilling mud may be used by a measurement system 111 to quantify concentration of additives in the drilling mud using LIBS. The measurement system 111 can be positioned on the surface 110 of the wellbore 118. The sample of drilling mud can be acquired from the mud tank 120 and can be processed by a fluid processing system 130 on the surface 110 of the wellbore 118 prior to additive quantification. The fluid processing system 130 may be used to perform centrifugation of the sample, coarse and fine filtration for the sample, distillation or selective flocculation of polymers or drill solids in the sample. Distillation can involve separating solids from liquids and retaining both the solid phase and the liquid phase for analysis. The coarse and fine filtration of the sample can involve filtering the sample into filtrate and filter-cake. Either the filtrate or the filter-cake may be analyzed by the measurement system 111 to quantify additives in the sample. The fluid processing system 130 may also be used to perform selective extraction, in which a solvent can be utilized that selectively extracts a compound of interest into the solvent, separating the compound of interest from other components of the drilling fluid. Any other type of processing may be performed on the sample.

In many examples, the processing may involve performing solid separation to remove solids above a certain size from the sample. The remaining liquid sample, which may include nanoparticles suspended in the liquid sample, can be analyzed by the measurement system 111 to quantify additives. Additionally or alternatively, the solids separated from the liquid portion of the sample may be analyzed by the measurement system 111 to quantify additives. In some examples, the fluid processing system 130 may also be used to dehydrate a sample (e.g., a whole mud sample, a filtered or centrifuged mud sample, a filtered mud sample, etc.). The dehydrated sample can be created by placing the sample under a vacuum element, a heating element, or a combination thereof. Dehydrating the sample may concentrate a particular compound of interest present in an additive. In some examples, whole, unprocessed mud (e.g., mud taken directly from the mud tank 120) may instead be analyzed by the measurement system 111.

The measurement system 111 may be or may include a LIBS device that can detect elements and compounds in the processed sample. The LIBS device is further described below with respect to FIG. 2. In some examples, the measurement system 111 and the fluid processing system 130 may be integrated into a single system that may also be automated. In other examples, the measurement system 111 and the fluid processing system 130 may be separate. In some examples, portions of the measurement system 111 or the fluid processing system 130 may be portable. For example, the LIBS device may be a handheld device.

Although the measurement system 111 is depicted in a drilling environment with drilling mud, in some examples, the measurement system 111 may be used in other contexts and with other types of fluids, such as fracturing fluids in fracturing environments, cementing fluids in completion environments, aqueous fluids, non-aqueous fluids, or any other types of fluids used in wellbore operations.

Figure 2:
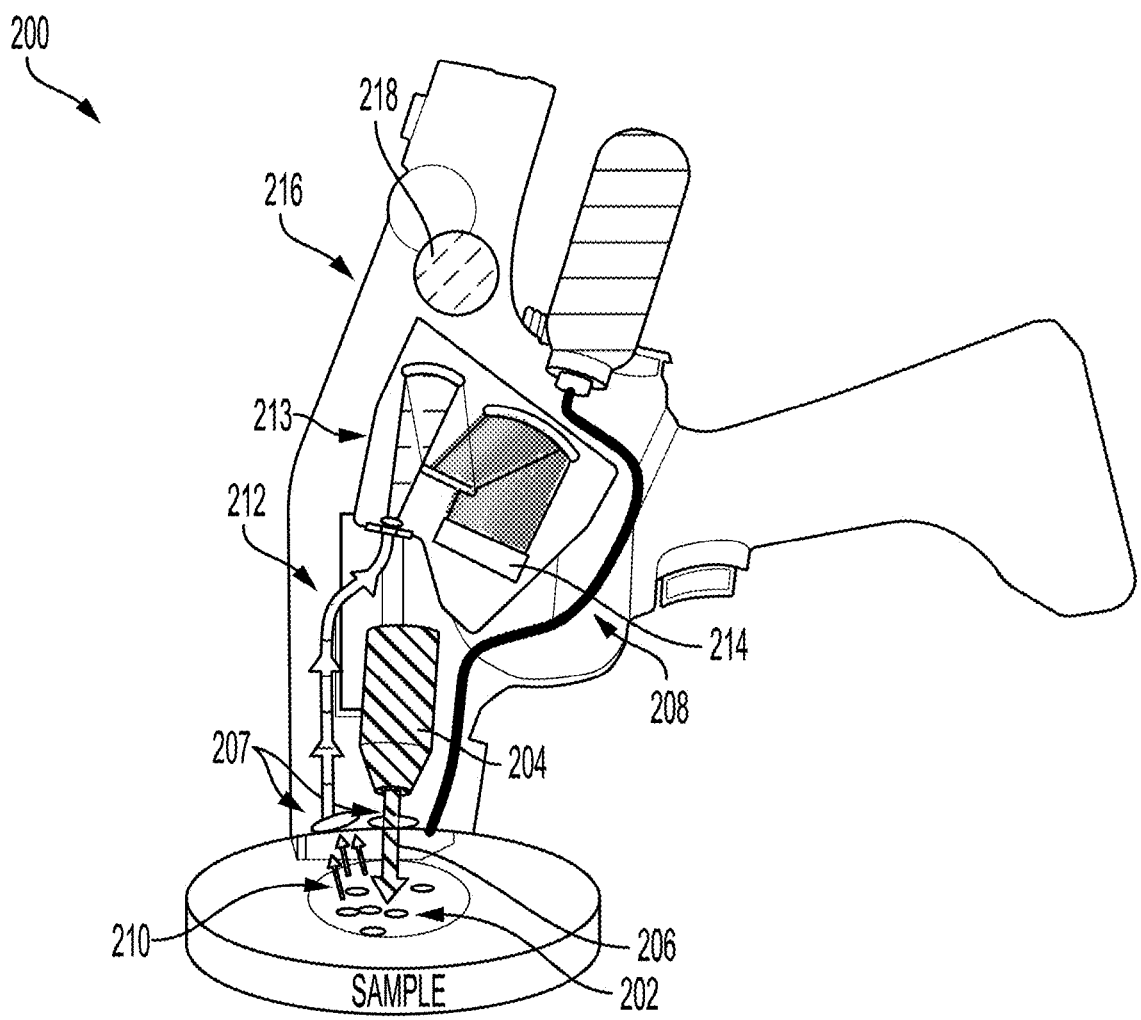
FIG. 2 is a cross-sectional view of a laser induced breakdown spectroscopy device for quantifying additives in wellbore fluid according to one example of the present disclosure.

FIG. 2 is a cross-sectional view of a laser induced breakdown spectroscopy (LIBS) device 200 for quantifying additives in wellbore fluid according to one example of the present disclosure. The LIBS device 200 depicted in FIG. 2 can be a handheld, portable device, but stationary LIBS devices may also be used.

The LIBS device 200 can be pointed at a sample 202 of wellbore fluid, which may be processed or unprocessed. In one example, the sample 202 may be active drilling fluid acquired from a wellbore. The LIBS device 200 can include a light source 204 such as a laser that can emit a first light beam 206 towards the sample 202. The first light beam 206 may travel through a focusing lens 207 to focus the first light beam 206 onto the sample 202. The first light beam 206 may be a highly energetic pulse that can ablate a surface of the sample 202 to form a plasma that atomizes and excites the sample 202. In some examples, the LIBS device 200 can include a supply of argon 208 that can stabilize and promote the plasma formation. The excitation of the sample 202 can generate a second light beam 210 that can be captured by the LIBS device 200.

For example, the second light beam 210 can be directed through the focusing lens 207 to be detected by an optical fiber 212 in the LIBS device 200. The optical fiber 212 can transmit the second light beam 210 to a spectrometer 213 in the LIBS device 200 that includes a charged coupled device (CCD) 214. The spectrometer 213 can sort the second light beam 210 by wavelength to generate a spectrum of optical data for the sample 202. In some examples, the LIBS device 200 may transmit the optical data to a computing device (not pictured) that can generate a detailed compositional analysis of the optical data. In other examples, the LIBS device 200 may include a central processing unit (CPU) 218 that can generate the compositional analysis.

For example, the CPU 218 can use the optical data to quantify an amount or concentration of particular additives in the sample 202. The LIBS device 200 may be used in two modes. A first mode can involve elemental analysis, in which individual elements can be detected and quantified. A second mode can involve chemical fingerprinting, in which relative amounts of elements in a specific compound (e.g., of an additive) can be measured. The CPU 218 can quantify the amount or the concentration of the compound present in the sample 202. In some examples, the CPU 218 may also quantify isotopic differences in the sample 202 that can further be used to develop a fingerprint for a given compound.

In some examples, the quantification of the additive determined by the CPU 218 can be output on a display 216 such as a liquid crystal display (LCD) of the LIBS device 200. A user can use the displayed concentration or amount of additive to adjust the composition of the wellbore fluid. Additionally or alternatively, the CPU 218 can determine an adjustment to the wellbore fluid based on the amount or concentration of the additive in the sample 202. For example, if a concentration of a particular additive is below a threshold amount, the adjustment can involve injecting additional additive into drilling mud circulating in a wellbore. In some examples, the CPU 218 may output a command to automatically adjust composition of the wellbore fluid, such as to a controller of the mud tank 120 depicted in FIG. 1.

In some examples, the sample 202 of wellbore fluid may include additives that have been tagged with particular atoms or molecules. Tags may be unique atoms or molecules that are not otherwise present in the wellbore fluid or additives, such as fluorine or phosphorus. Tagging an additive may improve detection by the LIBS device 200 of the additive in the sample. For example, an additive may be a polymer that is typically built with a single monomer. During polymerization of the polymer, the additive can be doped with a small percentage of another monomer that is covalently bonded to the tag. The resulting polymer of the additive can have a few tagged atoms attached. These tagged atoms may be distinctive and can be easily identified by the LIBS device 200.

Figure 3:
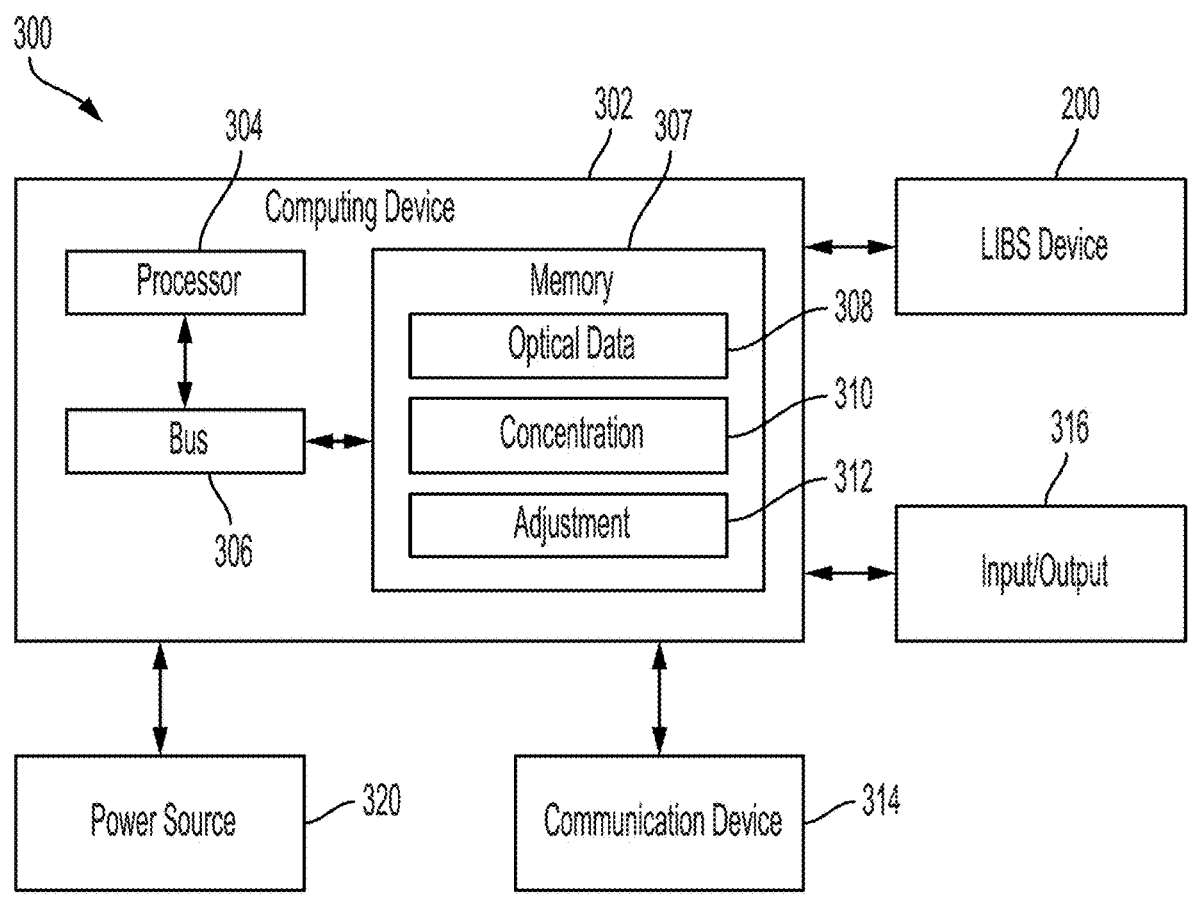
FIG. 3 is a block diagram of a computing system for quantifying additives in wellbore fluid based on a laser induced breakdown spectroscopy measurement according to one example of the present disclosure.

FIG. 3 is a block diagram of a computing system 300 for quantifying additives in wellbore fluid based on a laser induced breakdown spectroscopy measurement according to one example of the present disclosure. In one or more examples, the components shown in FIG. 3 (e.g., the computing device 302, power source 320, the communications device 314, the input/output interface 316, and the LIBS device 200) may be integrated into a single structure. For example, the components may be within a single housing, such as within the measurement system 111 of FIG. 1. In other examples, the components shown in FIG. 3 may be distributed (e.g., in separate housings) and in electrical communication with each other. In some examples, the computing device 302 may be integrated with the LIBS device 200 (e.g., as the CPU 218 of FIG. 2). In other examples, the computing device 302 may be communicatively coupled with the LIBS device 200.

The computing system 300 includes the computing device 302. The computing device 302 may include a processor 304, a memory 307, and a bus 306. The processor 304 may execute one or more operations for obtaining and analyzing optical data 308 associated with wellbore fluid from the LIBS device 200. The processor 304 may execute instructions stored in the memory 307 to perform the operations. The processor 304 may include one processing device or multiple processing devices. Non-limiting examples of the processor 304 include a Field-Programmable Gate Array (FPGA), an application-specific integrated circuit (ASIC), a microprocessor, etc.

The processor 304 may be communicatively coupled to the memory 307 via the bus 306. The non-volatile memory 307 may include any type of memory device that retains stored information when powered off. Non-limiting examples of the memory 307 include electrically erasable and programmable read-only memory (EEPROM), flash memory, or any other type of non-volatile memory. In some examples, at least part of the memory 307 can include a medium from which the processor 304 can read instructions. A non-transitory computer-readable medium can include electronic, optical, magnetic, or other storage devices capable of providing the processor 304 with computer-readable instructions or other program code. Non-limiting examples of a computer-readable medium include (but are not limited to) magnetic disk(s), memory chip(s), ROM, random-access memory (RAM), an ASIC, a configured processor, optical storage, or any other medium from which a computer processor can read instructions. The instructions can include processor-specific instructions generated by a compiler or an interpreter from code written in any suitable computer-programming language, including, for example, C, C++, C#, etc.

In some examples, the memory 307 may include computer program instructions for executing processes that involve determining concentrations 310 of additives in samples of wellbore fluid based on optical data 308 acquired by a LIBS device 200. The processes may rely, at least in part, on optical data 308 located within the memory 307. The memory 307 may also include computer program instructions for executing processes that involve determining an adjustment 312 to a wellbore fluid based on the concentration 310 of an additive detected from the optical data 308.

The computing system 300 may include a power source 320. The power source 320 may be in electrical communication with the computing device 302 and the communication device 314. The communication device 314 may be connected to wellbore equipment used for formation, stimulation, or production. In some examples, the power source 320 may include a battery or an electrical cable (e.g., a wireline). In some examples, the power source 320 may include an AC signal generator. The computing device 302 may operate the power source 320 to apply a signal to the communication device 144 to operate the equipment used for wellbore formation, wellbore stimulation, or wellbore production with controllable parameters, such as parameters for performing the adjustment 312 to the composition of the wellbore fluid. For example, the computing device 302 may cause the power source 320 to apply a voltage with a frequency within a specific frequency range to the communication device 144. In other examples, the computing device 302, rather than the power source 320, may apply the signal to the communication device 314.

The communication device 314 may include or may be coupled to a wireless communication system to control equipment remotely. In some examples, part of the communication device 314 may be implemented in software. For example, the communication device 314 may include instructions stored in the memory 307. The communication device 314 may receive signals from remote devices and transmit data to remote devices. For example, the communication device 314 may transmit wireless communications that are modulated by data. In some examples, the communication device 314 may receive signals (e.g., associated with data to be transmitted) from the processor 304 and may amplify, filter, modulate, frequency shift, and otherwise manipulate the signals.

The computing device 302 may receive input (e.g., the optical data 308) from the LIBS device 200. The computing system 300 can also include input/output interface 316. Input/output interface 316 may connect to a keyboard, pointing device, display, and other computer input/output devices. An operator may provide input using the input/output interface 332. Such input may include confirmation that a concentration 310 of an additive is below a threshold amount, or confirmation that an adjustment 312 to the wellbore fluid should be performed (e.g., injecting an additional amount of additive into the wellbore fluid).

Figure 4:
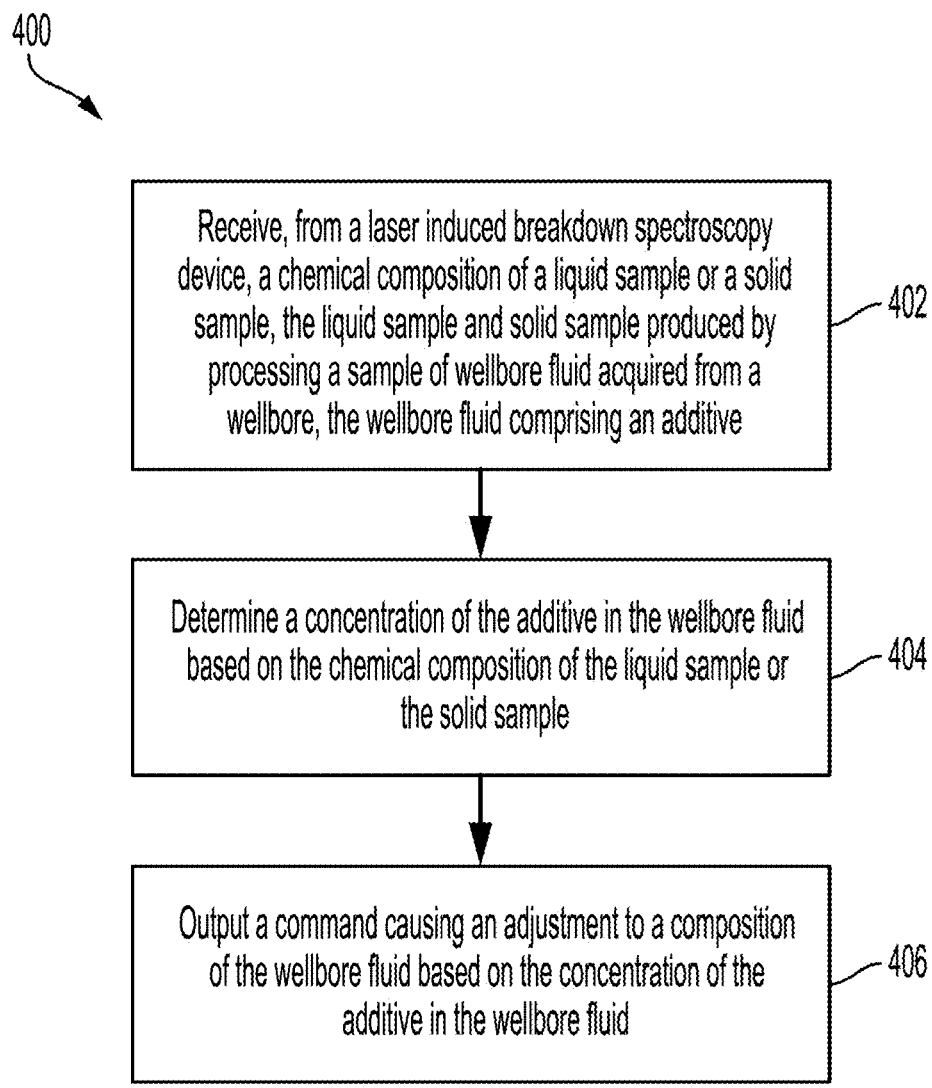
FIG. 4 is a flowchart describing a process for quantifying additives in wellbore fluid using laser induced breakdown spectroscopy measurements according to one example of the present disclosure.

FIG. 4 is a flowchart describing a process 400 for quantifying additives in wellbore fluid using laser induced breakdown spectroscopy (LIBS) measurements according to one example of the present disclosure. While the description of the process 400 provided below describes the process 400 with reference to drilling operations of the wellbore 118, it may be appreciated by those skilled in the art that the process 400 may also be applied to other oil and gas operations (e.g., stimulation of the wellbore 118, production from the wellbore 118, maintenance operations at the wellbore 118, etc.). The operations of process 400 are described with reference to the elements of FIGS. 1-3.

At block 402, the computing device 302 can receive, from a laser induced breakdown spectroscopy (LIBS) device 200, a chemical composition of a liquid sample or a solid sample. The liquid sample and the solid sample can be processed by processing a sample 202 of wellbore fluid acquired from a wellbore 118. For example, the sample 202 can be extracted from a mud tank 120. The wellbore fluid may be drilling fluid that has been actively circulating in the wellbore 118 prior to returning to the mud tank 120 at the surface 110 of the wellbore 118. The wellbore fluid can include one or more additives, such as viscosifiers, emulsifiers, or lubricants that were injected into the wellbore fluid. As the wellbore fluid circulates downhole, the concentration of the additives may change. For example, the wellbore fluid may acquire liquids, gases, or other materials from the subterranean formation 102, thus changing the concentration of any particular additive when acquired materials are filtered out of the wellbore fluid. A fluid processing system 130 can process the sample 202 to separate the wellbore fluid into a liquid sample or a solid sample. The separation can be performed via centrifugation, coarse filtration, fine filtration, selective flocculation, distillation or selective extraction of the sample. In some examples, the sample may be dehydrated via a vacuum or a heating element to concentrate compounds of interest within a certain additive. The fluid processing system 130 can be at the surface 110 of the wellbore 118. This can allow the sample to be processed onsite without requiring the sample to be transported to a laboratory at a secondary location.

The LIBS device 200 can identify a chemical composition of the liquid sample or the solid sample. In some examples, the LIBS device 200 can determine an elemental composition of the liquid sample or the solid sample. For example, a particular additive may be tagged with atoms of an element such as fluorine. The LIBS device 200 can be sensitive enough to detect the fluorine that may only be included in the particular additive. Additionally or alternatively, the LIBS device 200 can determine a chemical fingerprinting of the liquid sample or the solid sample. The chemical fingerprinting can be a chemical compound of an additive.

At block 408, the computing device 302 can determine a concentration 310 of the additive in the wellbore fluid based on the chemical composition of the liquid sample or the solid sample. The computing device 302 may be included in the measurement system 111 or the LIBS device 200, or may be a separate device that is communicatively coupled with the LIBS device 200. The computing device 302 may determine an adjustment 312 to a composition of the wellbore fluid based on the concentration 310 of the additive. For example, the computing device 302 can determine that the concentration 310 of the additive in the wellbore is lower than a predefined threshold. The computing device 302 can then determine an amount of the additive to inject into the wellbore fluid to cause the concentration of the additive in the wellbore fluid to exceed the predefined threshold.

At block 410, the computing device 302 can output a command causing an adjustment 312 to a composition of the wellbore fluid based on the concentration 310 of the additive in the wellbore fluid. For example, if the concentration 310 of the additive in the wellbore fluid is below the predefined threshold, the command can cause a controller of the mud tank 120 at the surface 110 of the wellbore 118 to inject the amount of additive determined by the computing device 302. In other examples, the computing device 302 may determine that the concentration of the additive is above a predefined threshold for the additive. In response, the computing device 302 can forgo outputting the command causing the adjustment 312.

In some aspects, method, system, and computer-readable medium for quantifying additives in wellbore fluid using laser induced breakdown spectroscopy are provided according to one or more of the following examples:

Example 1 is a system comprising: a fluid processing system usable to process a sample of wellbore fluid from a wellbore by separating the sample of the wellbore fluid into a liquid sample and a solid sample, the wellbore fluid comprising an additive; and a measurement system comprising: a laser induced breakdown spectroscopy device usable to identify a chemical composition of the liquid sample or the solid sample; a processor; and a memory that comprises instructions executable by the processor for causing the processor to: determine a concentration of the additive in the wellbore fluid based on the chemical composition of the liquid sample or the solid sample; and output a command causing an adjustment to a composition of the wellbore fluid based on the concentration of the additive in the wellbore fluid.

Example 2 is the system of example(s) 1, wherein the additive in the wellbore fluid comprises a tagged atom, and wherein the memory further comprises instructions executable by the processor for causing the processor to determine the concentration of the additive in the wellbore fluid by: detecting the tagged atom in optical data received from the laser induced breakdown spectroscopy device; and determining the concentration of the additive in the wellbore fluid based on a detected concentration of the tagged atom in the liquid sample or the solid sample.

Example 3 is the system of example(s) 1-2, wherein the memory further comprises instructions executable by the processor for causing the processor to: determine the adjustment to the composition of the wellbore fluid by: determining that the concentration of the additive in the wellbore fluid is lower than a predefined threshold; and determining an amount of additive to inject into the wellbore fluid to cause the concentration of the additive in the wellbore fluid to exceed the predefined threshold.

Example 4 is the system of example(s) 1-3, wherein the laser induced breakdown spectroscopy device is configurable to identify the chemical composition of the sample by determining an elemental composition or a chemical fingerprinting of the liquid sample or the solid sample.

Example 5 is the system of example(s) 1-4, wherein the fluid processing system is further usable to perform at least one of centrifugation, coarse filtration, fine filtration, distillation, selective flocculation, or selective extraction of the sample.

Example 6 is the system of example(s) 1-5, wherein the memory further comprises instructions that are executable by the processor for causing the processor to: determine that the concentration of the additive in the wellbore fluid exceeds a predefined threshold for the additive; and forgo outputting the command causing the adjustment in response to determining that the concentration of the additive in the wellbore exceeds the predefined threshold.

Example 7 is the system of example(s) 1-6, wherein the additive comprises at least one of a shale inhibitor, a fluid loss additive, a viscosifier, a suspension aide, a corrosion inhibitor, an emulsifier, a bridging agent, a weighting agent, a salt, a glycol, a silicate, a nanoparticle, loss circulation materials, or a lubricant.

Example 8 is a method comprising: receiving, from a laser induced breakdown spectroscopy device, a chemical composition of a liquid sample or a solid sample, the liquid sample and solid sample produced by processing a sample of wellbore fluid acquired from a wellbore, the wellbore fluid comprising an additive; determining a concentration of the additive in the wellbore fluid based on the chemical composition of the liquid sample or the solid sample; and causing an adjustment to a composition of the wellbore fluid based on the concentration of the additive in the wellbore fluid.

Example 9 is the method of example(s) 8, wherein the additive in the wellbore fluid comprises a tagged atom, and wherein the method further comprises determining the concentration of the additive in the wellbore fluid by: detecting the tagged atom in optical data received from the laser induced breakdown spectroscopy device; and determining the concentration of the additive in the wellbore fluid based on a detected concentration of the tagged atom in the liquid sample or the solid sample.

Example 10 is the method of example(s) 8-9, further comprising: determining the adjustment to the composition of the wellbore fluid by: determining that the concentration of the additive in the wellbore fluid is lower than a predefined threshold; and determining an amount of additive to inject into the wellbore fluid to cause the concentration of the additive in the wellbore fluid to exceed the predefined threshold.

Example 11 is the method of example(s) 8-10, wherein the laser induced breakdown spectroscopy device is usable to identify the chemical composition by performing of at least one of determining an elemental composition or a chemical fingerprinting of the liquid sample or the solid sample.

Example 12 is the method of example(s) 8-11, wherein the sample is processed to generate the liquid sample and the solid sample by performing at least one of centrifugation, coarse filtration, fine filtration, distillation, selective flocculation, or selective extraction of the sample.

Example 13 is the method of example(s) 8-12, further comprising: determining that the concentration of the additive in the wellbore fluid exceeds a predefined threshold for the additive; and forgoing causing the adjustment in response to determining that the concentration of the additive in the wellbore exceeds the predefined threshold.

Example 14 is the method of example(s) 8-13, wherein the additive comprises at least one of a shale inhibitor, a fluid loss additive, a viscosifier, a suspension aide, a corrosion inhibitor, an emulsifier, a bridging agent, a weighting agent, a salt, a glycol, a silicate, a nanoparticle, loss circulation materials, or a lubricant.

Example 15 is a non-transitory computer-readable medium comprising program code that is executable by a processing device for causing the processing device to: identify, via laser induced breakdown spectroscopy, a chemical composition of a liquid sample or a solid sample, the liquid sample and the solid sample produced by processing a sample of wellbore fluid acquired from a wellbore, the wellbore fluid comprising an additive; determine a concentration of the additive in the wellbore fluid based on the chemical composition of the liquid sample or the solid sample; and output a command causing an adjustment to a composition of the wellbore fluid based on the concentration of the additive in the wellbore fluid.

Example 16 is the non-transitory computer-readable medium of example(s) 15, wherein the additive in the wellbore fluid comprises a tagged atom, and wherein the non-transitory computer-readable medium further comprises program code that is executable by the processing device for causing the processing device to determine the concentration of the additive in the wellbore fluid by: detecting the tagged atom in optical data received from a laser induced breakdown spectroscopy device; and determining the concentration of the additive in the wellbore fluid based on a detected concentration of the tagged atom in the liquid sample or the solid sample.

Example 17 is the non-transitory computer-readable medium of example(s) 15-16, wherein the non-transitory computer-readable medium further comprises program code that is executable by the processing device for causing the processing device to: determine the adjustment to the composition of the wellbore fluid by: determining that the concentration of the additive in the wellbore fluid is lower than a predefined threshold; and determining an amount of additive to inject into the wellbore fluid to cause the concentration of the additive in the wellbore fluid to exceed the predefined threshold.

Example 18 is the non-transitory computer-readable medium of example(s) 15-17, wherein a laser induced breakdown spectroscopy device is usable to identify the chemical composition by determining at least one of an elemental composition or a chemical fingerprinting of the liquid sample or the solid sample.

Example 19 is the non-transitory computer-readable medium of example(s) 15-18, wherein the sample is processed by performing at least one of centrifugation, coarse filtration, fine filtration, distillation, selective flocculation, or selective extraction of the sample.

Example 20 is the non-transitory computer-readable medium of example(s) 15-19, wherein the additive comprises at least one of a shale inhibitor, a fluid loss additive, a viscosifier, a suspension aide, a corrosion inhibitor, an emulsifier, a bridging agent, a weighting agent, a salt, a glycol, a silicate, a nanoparticle, loss circulation materials, or a lubricant.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
   processing a sample of wellbore fluid acquired from a wellbore into a liquid sample and a solid sample by performing filtration, selective flocculation, centrifugation, distillation, or selective extraction of the sample;
   receiving, from a laser induced breakdown spectroscopy device, a chemical composition of the liquid sample or the solid sample, the wellbore fluid comprising an additive;
   determining a concentration of the additive in the wellbore fluid based on the chemical composition of the liquid sample or the solid sample; and
   causing an adjustment to a composition of the wellbore fluid based on the concentration of the additive in the wellbore fluid.

2. The method of claim 1, wherein the additive in the wellbore fluid comprises a tagged atom, and wherein the method further comprises determining the concentration of the additive in the wellbore fluid by:
   polymerizing the additive with the tagged atom prior to injecting the additive into the wellbore fluid;
   detecting the tagged atom in optical data received from the laser induced breakdown spectroscopy device; and
   determining the concentration of the additive in the wellbore fluid based on a detected concentration of the tagged atom in the liquid sample or the solid sample.

3. The method of claim 1, further comprising:
   determining the adjustment to the composition of the wellbore fluid by:
      determining that the concentration of the additive in the wellbore fluid is lower than a predefined threshold; and
      determining an amount of additive to inject into the wellbore fluid to cause the concentration of the additive in the wellbore fluid to exceed the predefined threshold.

4. The method of claim 1, wherein the laser induced breakdown spectroscopy device is usable to identify the chemical composition by performing of at least one of determining an elemental composition or a chemical fingerprinting of the liquid sample or the solid sample.

5. The method of claim 1, wherein the sample is processed to generate the liquid sample and the solid sample by performing at least dehydration of the sample.

6. The method of claim 1, further comprising:
   determining that the concentration of the additive in the wellbore fluid exceeds a predefined threshold for the additive; and
   forgoing causing the adjustment in response to determining that the concentration of the additive in the wellbore exceeds the predefined threshold.

7. The method of claim 1, wherein the additive comprises at least one of a shale inhibitor, a fluid loss additive, a viscosifier, a suspension aide, a corrosion inhibitor, an emulsifier, a bridging agent, a weighting agent, a salt, a glycol, a silicate, a nanoparticle, loss circulation materials, or a lubricant.

8. The method of claim 1, wherein the filtration comprises a first type of filtration and a second type of filtration that is different from the first type of filtration.

9. The method of claim 8, wherein the first type of filtration causes the liquid sample or the solid sample to have particles in a first size range, wherein the second type of filtration causes the liquid sample or the solid sample to have particles in a second size range, and wherein the first size range is larger than the second size range.

* * * * *